(12) United States Patent
Inochkin et al.

(10) Patent No.: US 7,274,155 B2
(45) Date of Patent: Sep. 25, 2007

(54) FLASH LAMP DRIVE CIRCUIT

(75) Inventors: Mikhail Inochkin, St. Petersburg (RU); Vycheslav V. Togatov, St. Petersburg (RU); Peter O. Gnatyuk, St. Petersburg (RU)

(73) Assignee: Palomar Medical Technologies, Inc., Burlington, MA (US)

( * ) Notice: Subject to any disclaimer, the term of this patent is extended or adjusted under 35 U.S.C. 154(b) by 0 days.

(21) Appl. No.: 11/091,270

(22) Filed: Mar. 28, 2005

(65) Prior Publication Data
US 2005/0168158 A1 Aug. 4, 2005

Related U.S. Application Data

(63) Continuation of application No. 10/600,167, filed on Jun. 20, 2003, now Pat. No. 6,888,319, which is a continuation-in-part of application No. 10/267,610, filed on Oct. 9, 2002, now abandoned, which is a continuation of application No. 09/797,501, filed on Mar. 1, 2001, now abandoned.

(51) Int. Cl.
*H05B 41/16* (2006.01)
(52) U.S. Cl. .............. 315/247; 315/246; 315/308; 315/291; 315/274
(58) Field of Classification Search ............. 315/247, 315/246, 308, 307, 291, 274, 224, 225, 209 R, 315/275, 273
See application file for complete search history.

(56) References Cited

U.S. PATENT DOCUMENTS 1,706,161 A    3/1929  Hollnagel
2,472,385 A    6/1949  Rollman
3,327,712 A    6/1967  Kaufman et al.

(Continued)

FOREIGN PATENT DOCUMENTS

AT    400305    4/1995

(Continued)

OTHER PUBLICATIONS

G.B. Altshuler et al., "Acoustic response of hard dental tissues to pulsed laser action," SPIE, vol. 2080, Dental Application of Lasers, pp. 97-103, 1993.

(Continued)

*Primary Examiner*—Tuyet Vo
(74) *Attorney, Agent, or Firm*—Thomas J. Engellenner; Deborah A. Miller; Nutter McClennen & Fish, LLP

(57) ABSTRACT

The invention provides a power supply or drive circuit for a pulsed flashlamp which utilizes a two-core component having common windings as both an inductor for arc mode drive and for breakdown triggering of the lamp. Discharge of a capacitor through the inductor and lamp is controlled by a high-speed semiconductor switch which is turned on and off by a suitable control, current flowing from the inductor through a one-way path including the lamp when the switch is off. The control maintains the ratio of the power variation through the lamp to the average power through the lamp substantially constant. The controls may also be utilized to control output pulse shape. Novel protective features are also provided for circuit components during turn on periods for the switch.

15 Claims, 5 Drawing Sheets

U.S. PATENT DOCUMENTS

| | | |
|---|---|---|
| 3,486,070 A | 12/1969 | Engel |
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,890,537 A * | 6/1975 | Park et al. .................. 315/208 |
| 3,900,034 A | 8/1975 | Katz |
| 3,913,002 A * | 10/1975 | Steigerwald et al. .......... 363/18 |
| 4,233,493 A | 11/1980 | Nath |
| 4,273,109 A | 6/1981 | Enderby |
| 4,275,335 A | 6/1981 | Ishida |
| 4,316,467 A | 2/1982 | Muckerheide |
| 4,388,924 A | 6/1983 | Weissman et al. |
| 4,456,872 A | 6/1984 | Froeschle |
| 4,461,294 A | 7/1984 | Baron |
| 4,524,289 A | 6/1985 | Hammond et al. |
| 4,539,987 A | 9/1985 | Nath et al. |
| 4,591,762 A | 5/1986 | Nakamura |
| 4,608,978 A | 9/1986 | Rohr |
| 4,617,926 A | 10/1986 | Sutton |
| 4,677,347 A | 6/1987 | Nakamura |
| 4,695,697 A | 9/1987 | Kosa |
| 4,718,416 A | 1/1988 | Nanaumi |
| 4,733,660 A | 3/1988 | Itzkan |
| 4,745,909 A | 5/1988 | Pelton et al. |
| 4,747,660 A | 5/1988 | Nishioka et al. |
| 4,749,913 A | 6/1988 | Stuermer et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,884,560 A | 12/1989 | Kuracina |
| 4,917,084 A | 4/1990 | Sinofsky |
| 4,926,227 A | 5/1990 | Jensen |
| 4,928,038 A | 5/1990 | Nerone |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,127,395 A | 7/1992 | Bontemps |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,267,399 A | 12/1993 | Johnston |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith |
| 5,522,813 A | 6/1996 | Trelles |
| 5,531,739 A | 7/1996 | Trelles |
| 5,531,740 A | 7/1996 | Black |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,655,547 A | 8/1997 | Karni |
| 5,658,323 A | 8/1997 | Miller |
| 5,660,836 A | 8/1997 | Knowlton |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A | 2/1998 | Eckhouse |
| 5,735,844 A | 4/1998 | Anderson et al. |
| 5,735,884 A | 4/1998 | Thompson et al. |
| 5,743,901 A | 4/1998 | Grove et al. |
| 5,755,751 A | 5/1998 | Eckhouse |
| 5,759,200 A | 6/1998 | Azar |
| 5,782,249 A | 7/1998 | Weber et al. |
| 5,810,801 A | 9/1998 | Anderson et al. |
| 5,814,008 A | 9/1998 | Chen et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,828,803 A | 10/1998 | Eckhouse |
| 5,830,208 A | 11/1998 | Muller |
| 5,836,999 A | 11/1998 | Eckhouse et al. |
| 5,840,048 A | 11/1998 | Cheng |
| 5,849,029 A | 12/1998 | Eckhouse et al. |
| 5,853,407 A | 12/1998 | Miller |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,913,883 A | 6/1999 | Alexander et al. |
| 5,944,748 A | 8/1999 | Mager et al. |
| 5,948,011 A | 9/1999 | Knowlton |
| 5,949,222 A | 9/1999 | Buono |
| 5,954,710 A | 9/1999 | Paolini et al. |
| 5,964,749 A | 10/1999 | Eckhouse et al. |
| 5,968,033 A | 10/1999 | Fuller |
| 5,968,034 A | 10/1999 | Fullmer et al. |
| 5,977,723 A | 11/1999 | Yoon |
| 6,015,404 A | 1/2000 | Altshuler et al. |
| 6,027,495 A | 2/2000 | Miller |
| RE36,634 E | 3/2000 | Ghaffari |
| 6,050,990 A | 4/2000 | Tankovich et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,096,029 A | 8/2000 | O'Donnell, Jr. |
| 6,096,209 A | 8/2000 | O'Brien et al. |
| 6,104,959 A | 8/2000 | Spertell |
| 6,120,497 A | 9/2000 | Anderson |
| 6,149,644 A | 11/2000 | Xie |
| 6,162,211 A | 12/2000 | Tankovich et al. |

| | | |
|---|---|---|
| 6,174,325 B1 | 1/2001 | Eckhouse |
| 6,197,020 B1 | 3/2001 | O'Donnell |
| 6,214,034 B1 | 4/2001 | Azar |
| 6,229,831 B1 | 5/2001 | Nightingale et al. |
| 6,235,016 B1 | 5/2001 | Stewart |
| 6,236,891 B1 | 5/2001 | Ingel et al. |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,290,713 B1 | 9/2001 | Russell |
| 6,306,130 B1 | 10/2001 | Anderson et al. |
| 6,319,274 B1 | 11/2001 | Shadduck |
| 6,350,276 B1 | 2/2002 | Knowlton |
| 6,354,370 B1 | 3/2002 | Miller et al. |
| 6,402,739 B1 | 6/2002 | Neev |
| 6,406,474 B1 | 6/2002 | Neuberger et al. |
| 6,436,094 B1 | 8/2002 | Reuter |
| 6,471,712 B2 | 10/2002 | Burres |
| 6,475,211 B2 | 11/2002 | Chess et al. |
| 6,508,813 B1 | 1/2003 | Altshuler |
| 6,511,475 B1 | 1/2003 | Altshuler et al. |
| 6,517,532 B1 | 2/2003 | Altshuler et al. |
| 6,605,080 B1 | 8/2003 | Altshuler et al. |
| 6,648,904 B2 | 11/2003 | Altshuler et al. |
| 6,653,618 B2 | 11/2003 | Zenzie |
| 6,663,620 B2 | 12/2003 | Altshuler et al. |
| 6,663,659 B2 | 12/2003 | McDaniel |
| 6,808,532 B2 | 10/2004 | Andersen et al. |
| 2001/0041886 A1 | 11/2001 | Durkin et al. |
| 2002/0005475 A1 | 1/2002 | Zenzie |
| 2002/0026225 A1 | 2/2002 | Segal |
| 2002/0091377 A1 | 7/2002 | Anderson |
| 2002/0123745 A1 | 9/2002 | Svaasand et al. |
| 2002/0128635 A1 | 9/2002 | Altshuler et al. |
| 2002/0161357 A1 | 10/2002 | Anderson |
| 2002/0173780 A1 | 11/2002 | Altshuler et al. |
| 2003/0023283 A1 | 1/2003 | McDaniel |
| 2003/0032950 A1 | 2/2003 | Altshuler et al. |
| 2003/0055414 A1 | 3/2003 | Altshuler et al. |
| 2003/0065314 A1 | 4/2003 | Altshuler et al. |
| 2004/0006332 A1 | 1/2004 | Black |

FOREIGN PATENT DOCUMENTS

| | | |
|---|---|---|
| AU | 1851583 | 3/1984 |
| DE | 3837248 | 5/1990 |
| EP | 0142671 | 5/1985 |
| EP | 0565331 | 10/1993 |
| EP | 0598984 | 6/1994 |
| EP | 0724894 | 8/1996 |
| EP | 0726083 | 8/1996 |
| EP | 0736308 | 10/1996 |
| EP | 0755698 | 1/1997 |
| EP | 0763371 | 3/1997 |
| EP | 0765673 | 4/1997 |
| EP | 0765674 | 4/1997 |
| EP | 0783904 | 7/1997 |
| EP | 0885629 | 12/1998 |
| EP | 1038505 | 9/2000 |
| EP | 1219258 | 7/2002 |
| EP | 1226787 | 7/2002 |
| EP | 1 457 234 A2 | 9/2004 |
| FR | 2199453 | 4/1974 |
| FR | 2591902 | 6/1987 |
| GB | 2044908 | 10/1980 |
| GB | 2123287 | 2/1984 |
| GB | 2360946 | 10/2001 |
| JP | 2001145520 | 5/2001 |
| RU | 2082337 | 6/1997 |
| RU | 2089126 | 10/1997 |
| RU | 2089127 | 10/1997 |
| RU | 2096051 | 11/1997 |
| RU | 2122848 | 10/1998 |
| WO | WO86/02783 | 5/1986 |
| WO | WO90/00420 | 1/1990 |
| WO | WO92/16338 | 1/1992 |
| WO | WO92/19165 | 11/1992 |
| WO | WO93/05920 | 4/1993 |
| WO | WO95/15725 | 6/1995 |
| WO | WO95/32441 | 11/1995 |
| WO | WO96/23447 | 8/1996 |
| WO | WO96/25979 | 8/1996 |
| WO | WO97/13458 | 4/1997 |
| WO | WO98/04317 | 2/1998 |
| WO | WO98/24507 | 6/1998 |
| WO | WO98/51235 | 11/1998 |
| WO | WO98/52481 | 11/1998 |
| WO | WO99/27997 | 6/1999 |
| WO | WO99/29243 | 6/1999 |
| WO | WO99/38569 | 8/1999 |
| WO | WO99/46005 | 9/1999 |
| WO | WO9949937 | 10/1999 |
| WO | WO 00/3257 | 1/2000 |
| WO | WO 00/43070 | 7/2000 |
| WO | WO 00/71045 | 11/2000 |
| WO | WO 00/78242 | 12/2000 |
| WO | WO 0074781 | 12/2000 |
| WO | WO 01/03257 | 1/2001 |
| WO | WO 01/26573 | 4/2001 |
| WO | WO 01/34048 | 5/2001 |
| WO | WO 01/42671 | 6/2001 |
| WO | WO 01/54606 | 8/2001 |
| WO | WO 02/53050 | 7/2002 |
| WO | WO 02/094116 | 11/2002 |

OTHER PUBLICATIONS

G.B. Altshuler et al., "Extended theory of selective photothermolysis," Lasers in Surgery and Medicine, vol. 29, pp. 416-432, 2001.

R.L. Amy & Storb, "Selective mitochondrial damage by a ruby laser microbeam: An electron microscopy study," Science, vol. 15, pp. 756-758, Nov. 1965.

R.R. Anderson et al., "The optics of human skin," Journal of Investigative Dermatology, vol. 77, No. 1, pp. 13-19, 1981.

R.R. Anderson & J.A. Parrish, "Selective photothermolysis: Precise microsurgery by selective absorption of pulsed radiation," Science, vol. 220, pp. 524-527, Apr. 1983.

A.V. Belikov et al., "Identification of enamel and dentine under tooth laser treatment," SPIE vol. 2623, Progress in Biomedical Optics Europe Series, Proceedings of Medical Applications of Lasers III, pp. 109-116, Sep. 1995.

P. Bjerring et al., "Selective Non-Ablative Wrinkle Reduction by Laser," J Cutan Laser Ther, vol. 2, pp. 9-15, 2000.

J.S. Dover et al., "Pigmented guinea pig skin irradiated with Q-switched ruby laser pulses," Arch Dermatol, vol. 125, pp. 43-49, Jan. 1989.

L.H. Finkelstein & L.M. Blastein, "Epilation of hair-bearing urethral grafts using the neodymium:yag surgical laser," Journal of Urology, vol. 146, pp. 840-842, Sep. 1991.

L. Goldman, Biomedical Aspects of the Laser, Springer-Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

L. Goldman, "Effects of new laser systems on the skin," Arch Dermatol., vol. 108, pp. 385-390, Sep. 1973.

L. Goldman, "Laser surgery for skin cancer," New York State Journal of Medicine, pp. 1897-1900, Oct. 1977.

L. Goldman, "Surgery by laser for malignant melanoma," J. Dermatol. Surg. Oncol., vol. 5, No. 2, pp. 141-144, Feb. 1979.

L. Goldman, "The skin," Arch Environ Health, vol. 18, pp. 434-436, Mar. 1969.

L. Goldman & D.F. Richfield, "The effect of repeated exposures to laser beams," Acta derm.-vernereol., vol. 44, pp. 264-268, 1964.

L. Goldman & R.J. Rockwell, "Laser action at the cellular level," JAMA, vol. 198, No. 6, pp. 641-644, Nov. 1966.

L. Goldman & R.G. Wilson, "Treatment of basal cell epithelioma by laser radiation," JAMA, vol. 189, No. 10, pp. 773-775.

L. Goldman et al., The biomedical aspects of lasers, JAMA, vol. 188, No. 3, pp. 302-306, Apr. 1964.

L. Goldman et al., "Effect of the laser beam on the skin, Preliminary report" Journal of Investigative Dermatology, vol. 40, pp. 121-122, 1963.

L. Goldman et al., "Effect of the laser beam on the skin, III. Exposure of cytological preparations," Journal of Investigative Dermatology, vol. 42, pp. 247-251, 1964.

L. Goldman et al., "Impact of the laser on nevi and melanomas," Archives of Dermatology, vol. 90, pp. 71-75, Jul. 1964.

L. Goldman et al., "Laser treatment of tattoos, A preliminary survey of three year's clinical experience," JAMA, vol. 201, No. 11, pp. 841-844, Sep. 1967.

L. Goldman et al., "Long-term laser exposure of a senile freckle," ArchEnviron Health, vol. 22, pp. 401-403, Mar. 1971.

L. Goldman et al., "Pathology, Pathology of the effect of the laser beam on the skin," Nature, vol. 197, No. 4870, pp. 912-914, Mar. 1963.

L. Goldman et al., "Preliminary investigation of fat embolization from pulsed ruby laser impacts of bone," Nature, vol. 221, pp. 361-363, Jan. 1969.

L. Goldman et al., "Radiation from a Q-switched ruby laser, Effect of repeated impacts of power output of 10 megawatts on a tattoo of man," Journal of Investigative Dermatology, vol. 44, pp. 69-71, 1965.

L. Goldman et al., "Replica microscopy and scanning electron microscopy of laser impacts on the skin," Journal of Investigative Dermatology, vol. 52, No. 1, pp. 18-24, 1969.

M.C. Grossman et al., "Damage to hair follicles by normal-mode ruby laser pulses," Journal of he American Academy of Dermatology, vol. 35, No. 6, pp. 889-894, Dec. 1996.

E. Klein et al., "Biological effects of laser radiation 1., "Northeast Electronics Research and Engineering Meeting, NEREM Record, IEEE catalogue No. F-60, pp. 108-109, 1965.

J.G. Kuhns et al., "Laser injury in skin," Laboratory Investigation, vol. 17, No. 1, pp. 1-13, Jul. 1967.

J.G. Kuhns et al., "Biological effects of laser radiation II Effects of laser irradiation on the skin," NEREM Record, pp. 152-153, 1965.

R.J. Margolis et al., "Visible action spectrum for melanin-specific selective photothermolysis," Lasers in Surgery and Medicine, vol. 9, pp. 389-397, 1989.

J.A. Parrish, "Selective thermal effects with pulsed irradiation from lasers: From organ to organelle," Journal of Investigative Dermatology, vol. 80, No. 6 Supplement, pp. 75s-80s, 1983.

L. Polla et al., "Malanosomes are a primary target of Q-switched ruby laser irradiation in guinea pig skin," Journal of Investigative Dermatology, vol. 89, No. 3, pp. 281-286, Sep. 1987.

T. Shimbashi & T. Kojima, "Ruby laser treatment of pigmented skin lesions," Aesth. Plast. Surg., vol. 19, pp. 225-229, 1995.

Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

C.R. Taylor et al., "Treatment of tattoos by Q-switched ruby laser," Arch. Dermatol. vol. 126, pp. 893-899, Jul. 1990.

V.V. Tuchin, "Laser light scattering in biomedical diagnostics and therapy," Journal of Laser Applications, vol. 5, No. 2-3, pp. 43-60, 1993.

S. Watanabe et al, "Comparative studies of femtosecond to microsecond laser pulses on selective pigmented cell injury in skin," Photochemistry and Photobiology, vol. 53, No. 6, pp. 757-762, 1991.

A.J. Welch et al., "Evaluation of cooling techniques for the protection of the pidermis during HD-yag laser irradiation of the skin," Neodymium-Yag Laser in Medicine and Surgery, Elsevier Science Publishing Co., publisher, pp. 195-204, 1983.

R.B. Yules et al., "The effect of Q-switched ruby laser radiation on dermal tattoo pigment in man," Arch Surg, vol. 95, pp. 179-180, Aug. 1967.

E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.

Abstracts Nos. 17-19, Lasers in Surgery and Medicine, ASLMS, Supplement 13, 2001.

Abstracts Nos. 219-223, ASLMS.

Abstracts, various.

Invention description to certificate of authorship, No. 532304, "The way of Investigation of radiation time structure of optical quantum generator".

Invention description to certificate of authorship, No. 719439, "The ring resonator of optical quantum generator".

Invention description to certificate of authorship, No. 741747, "The modulator of optical radiation intensity".

Invention description to certificate of authorship, No. SU 1257475 A1, "Laser interferometric device to determine no-linearity of an index of refraction of optical medium".

Invention description to certificate of authorship, No. SU 1326962 A1, "The way of determination of non-linearity of an index of refraction of optical medium".

\* cited by examiner

FLASH LAMP DRIVE CIRCUIT

CROSS-REFERENCE TO RELATED APPLICATIONS

This application is a continuation of U.S. patent application Ser. No. 10/600,167, filed Jun. 20, 2003 now U.S. Pat. No. 6,888,319, which is a continuation-in-part of U.S. patent application Ser. No. 10/267,610, filed Oct. 9, 2002, now abandoned entitled "Flashlamp Drive Circuit" by Mikhail Inochkin, Vycheslav V. Togatov, and Peter O. Gnatyuk, which is a continuation of U.S. patent application Ser. No. 09/797,501, filed Mar. 1, 2001 now abandoned, entitled "Flashlamp Drive Circuit" by Mikhail Inochkin, Vycheslav V. Togatov, and Peter O. Gnatyuk, all of which are incorporated herein by reference in their entirety.

FIELD OF THE INVENTION

This invention relates to pulsed flashlamps and more particularly to improved drive circuits for such flashlamps.

BACKGROUND OF THE INVENTION

Pulsed flashlamps, and in particular Xe filled flashlamps, are used in a variety of applications, including to pump various gas or other laser devices, in various photo, copying, optical detection and optical ranging applications, in cosmetology and in various dermatology and other medical applications. Such lamps normally operate at comparatively high peak voltage, current, and light intensity/power. In order to achieve such high values, power supplies or drives for such lamps typically employ a storage capacitor, which is charged between lamp flashes or pulses, in series with an inductor and some type of switch. Examples of switches used in the past have included thyristors, which once turned on, generally remain on until the capacitor has fully discharged, and transistors. Circuits, such as disclosed in U.S. Pat. No. 4,524,289, which are a modified version of the more standard circuits indicated above, have also been used for driving flashlamps, the primary advantage of such circuits being that they require a smaller capacitor for a given flashlamp having particular voltage and current requirements. U.S. Pat. No. 4,275,335 teaches a flash lamp drive circuit which detects flash lamp current or voltage to control capacitor discharge to maintain substantially constant light intensity.

However, none of the prior art circuits have the capability of producing quickly changing programmable pulse shapes for the flashlamp output, none of these circuits provide protection for circuit components during switch turn-on transitions, something which is generally required for high powered lamp applications, and none of the current circuits are capable of maintaining constant power output from the lamp, and thus constant lamp intensity, when there are fluctuations in lamp impedance, such fluctuations occurring, and sometimes being substantial, as a result of changes in lamp temperature, and as a result of other factors.

Further, with the possible exception of the "335" patent, in none of these circuits is it feasible to produce flashlamp pulses of longer than several milliseconds, the latter problem resulting from the fact that the size of the capacitor utilized increases substantially linearly with pulse width and becomes prohibitively large for most applications beyond a few milliseconds. The size of the required capacitor for a given output is also increased by the relatively low efficiency in capacitor utilization in most of these prior art circuits, such circuits generally utilizing only 20-50% of the energy stored in the capacitor. However, there are applications, particularly medical applications, where the shape of the optical pulses is important in order to achieve a desired therapeutic effect, and in particular to achieve such effect without damage to areas of the patient's body not being treated. For example, in optical dermatology, it may be desirable to rapidly heat a target chromophore to a selected temperature, and to then reduce applied energy so as to maintain the chromophore at the desired temperature. There are also applications where pulses well in excess of a few milliseconds, for example on the order of several hundred milliseconds, may be desirable. The advantages of such long pulses in performing various optical medical procedures, including optical dermatology, is discussed in co-pending application Ser. No. 09/769,960, filed Jan. 25, 2001 and entitled METHOD AND APPARATUS FOR MEDICAL TREATMENT UTILIZING LONG DURATION ELECTROMAGNETIC RADIATION. Flashlamps are one potential source of optical radiation in such applications.

Finally, more efficient utilization of energy stored in the capacitor, which permits the use of smaller capacitors carrying lesser charge, is desirable in all flashlamp applications since it reduces the size, weight and cost of the lamp drive circuitry and enhances the safety of such drive circuits by reducing shock risks. An efficient drive circuit for flashlamps which permits pulses in excess of several milliseconds to be generated without requiring an excessively large capacitor and/or fast, programmable control of pulse shape is therefore desirable.

Another problem with flashlamps is that, in order to avoid premature failure of the lamp, it is desirable that discharge first be established in a low current density simmer mode prior to transfer to an arc mode. This is generally accomplished by triggering to initiate breakdown in the lamp with a triggering circuit, maintaining discharge with a low current DC simmer source and then providing the main current discharge for arc mode from completely separate circuitry. This duplication of components increases the size, weight and cost of flashlamp drive circuits; however, circuitry for permitting sharing of components for at least some of these functions does not currently exist.

SUMMARY OF THE INVENTION

In accordance with the above, this invention provides, for one aspect thereof, a drive circuit for a pulsed flashlamp which includes a capacitor chargeable to a voltage sufficient, when applied across said lamp, to maintain a desired optical output in arc mode, an inductor connected in series with the lamp, a high-speed semiconductor switch connected to, when off, block discharge of the capacitor and to, when on, permit discharge of the capacitor through the inductor and lamp, a one-way path for current flow from the inductor through the lamp at least when the switch is off, a sensor for current through the lamp and a control operative in response to the sensor for controlling the on/off state of the switch to maintain relative power deviation $\alpha = \Delta P/P_0$ through the lamp substantially constant over a desired range of average pulsed lamp powers $P_0$. In the equation, power ripple $\Delta P = P_{max} - P_{min}$, $$P_o = \frac{P_{max} + P_{min}}{2}$$

and $P_{max}$ and $P_{min}$ are maximum and minimum power, respectively, of lamp hysteresis. Thus $\Delta P$ is high when $P_0$ is high and is low when $P_0$ is low. The control may have a reference voltage $V_{ref}$ applied thereto, $V_{ref}$ being a function of the selected $P_0$. The control compares a function of $V_{ref}$ against a voltage function of the sensor output to control the on/off state of the switch. The switch may be turned off when the function of sensor output is greater than a first function of $V_{ref}(V_{ref1})$ and is turned on when the function of sensor output is less than a second function of $V_{ref}(V_{ref2})$, where $V_{ref1} > V_{ref2}$. The control may include a comparator having $V_{ref}$ applied as one input and an output from the sensor applied as a second input, the comparator being configurable to achieve a desired power ripple or hysteresis $\Delta P$. The comparator may include a difference amplifier, $V_{ref}$ being applied to one input of the amplifier through a reconfigurable first voltage divider, and the output from the sensor may be applied to a second input of the amplifier through a second voltage divider. The first voltage divider is normally configured to provide $V_{ref1}$ to the amplifier, and may be reconfigured in response to an output from the amplifier when the switch is off to provide $V_{ref2}$ to the amplifier. Alternatively, the comparitor may include an error amplifier, Vref being applied to one input of the error amplifier and the output from the sensor being applied to a second input of the error amplifier, the output from the error amplifier being applied through a reconfigurable voltage divider to one input of a difference amplifier, and a voltage indicative of lamp current being applied to a second input of the difference amplifier. The voltage divider is normally configured to provide Vref1 to the difference amplifier and is reconfigured when the switch is off to provide Vref2 to the difference amplifier. The lamp normally generates output pulses of a duration $t_p$, with the switch being turned on and off multiple times during each output pulse. The capacitor is normally recharged between output pulses. The control may include a control which selectively varies $V_{ref}$ during each output pulse to achieve a selected output pulse shape. The one-way path may include a diode in a closed loop with the inductor and lamp, the inductor maintaining current flow through the lamp and diode when the switch is off. A mechanism may be provided which inhibits current flow through the diode from the switch during transition periods when the switch is being turned on and the diode is being turned off, this mechanism being a saturable inductor in series with the diode for preferred embodiments, and a saturable inductor may also be provided in series with the switch to inhibit current flow through the switch during such transition periods.

The inductor preferably includes an inductance or load coil wound on a magnetic core which is non-saturating for the operating range of the drive circuit, which core may for example be formed of powdered iron. The coil preferably has a plurality of windings and is also wound on a second core having low losses at high frequency. A primary coil having a number of windings which is a small fraction of the plurality of windings of the inductance coil is wound at least on the second core and a circuit is provided for selectively applying a voltage to the primary coil, the voltage resulting in a stepped up trigger voltage in the inductance coil, which trigger voltage is applied to initiate breakdown in the lamp. The second core is preferably of a linear ferrite material. A DC simmer current source may also be connected to sustain the lamp in a low current glow or simmer mode when the lamp is not in arc mode. Various of the above features, including the features of this paragraph, may be utilized either in conjunction with other features of the invention or independent thereof.

BRIEF DESCRIPTION OF THE DRAWINGS

The foregoing and other objects, features and advantages of the invention will be apparent from the following more particular description of preferred embodiments of the invention as illustrated in the accompanying drawings, the same or related reference numerals being used for like elements in the various drawings.

DETAILED DESCRIPTION

Figure 1:
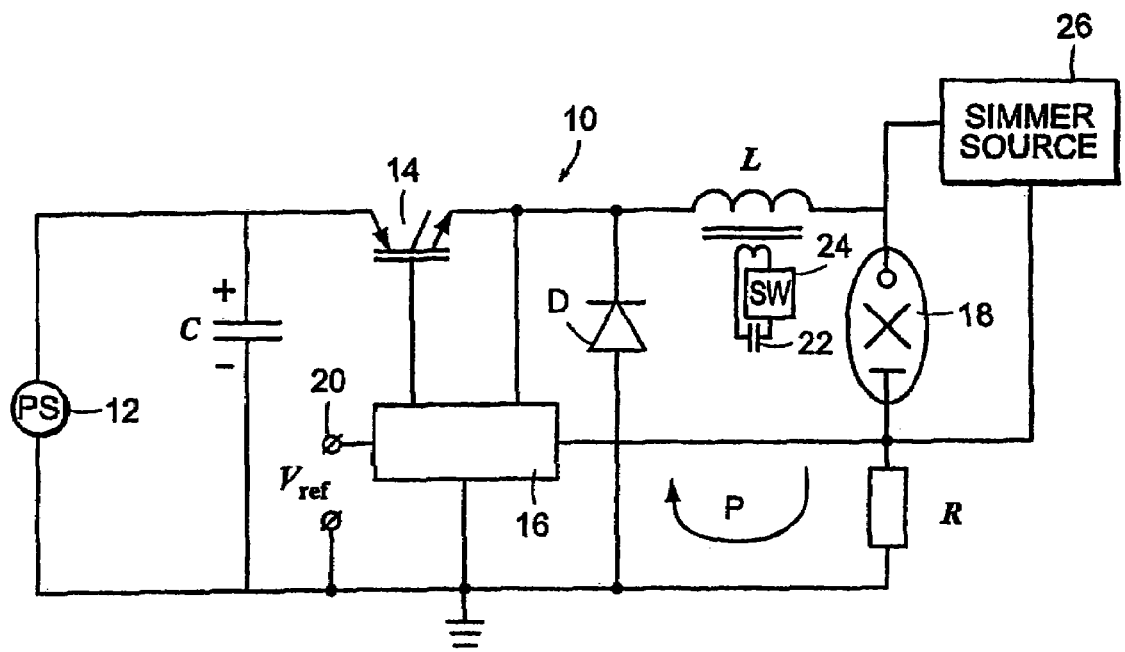
FIG. 1 is a schematic semi-block diagram of a circuit incorporating some of the teachings of this invention.

Referring first to FIG. 1, a pulsed flashlamp drive circuit 10 is shown for an illustrative embodiment of the invention. The circuit includes a capacitor C which is connected to be charged from a suitable power source 12. Power source 12 may be a 120 V, 240 V or other suitable line current, which may be suitably rectified or otherwise processed, may be a battery, or may be some other suitable power source. For illustrative embodiments, charge current from source 12 is only a few amps, for example one to two amps. A standard control circuit (not shown), including a switch, is provided to charge capacitor C to a selected preset voltage E and to prevent overvoltage. Capacitor C discharges through a high speed power switch transistor 14 which is connected to be driven from a control circuit 16, an exemplary such circuit being shown in FIG. 2. The output from switch 14 is applied through an inductor L to one side of pulsed flashlamp 18. The other side of flashlamp 18 is connected through a high speed current sensor to ground. The current sensor may be a resistor R as shown in FIG. 1, may be a Hall effect device, or may be some other suitable current sensor. The junction of flashlamp 18 and the resistor R is connected as a feedback input to control circuit 16 and a reference voltage $V_{ref}$ is applied through terminal 20 as a second input to the control circuit. Where the current sensor is not a resistor, the feedback signal to the control circuit would be obtained from a point in the circuit appropriate for the sensor used. A free wheeling diode D, for example a high power diode with soft recovery, is connected between ground and the input side of inductor L, providing a closed loop path P for current flow from the coil through flashlamp 18, resistor R and diode D. As will be discussed in conjunction with FIG. 3, inductor L may include a multi-turn coil wound on a pair of adjacent cores, one of which functions as the core of a step-up transformer to induce a high voltage trigger pulse or signal for application to lamp 18. The trigger signal comes from a capacitor 22 under control of a switch 24. A simmer current source 26 is also provided to maintain low current glow discharge of lamp 18 when the lamp is not in arc mode. Source 26 is typically a very low current source, typically less than one amp, and as little as a tenth of a amp or less for an illustrative embodiment.

Figure 2:
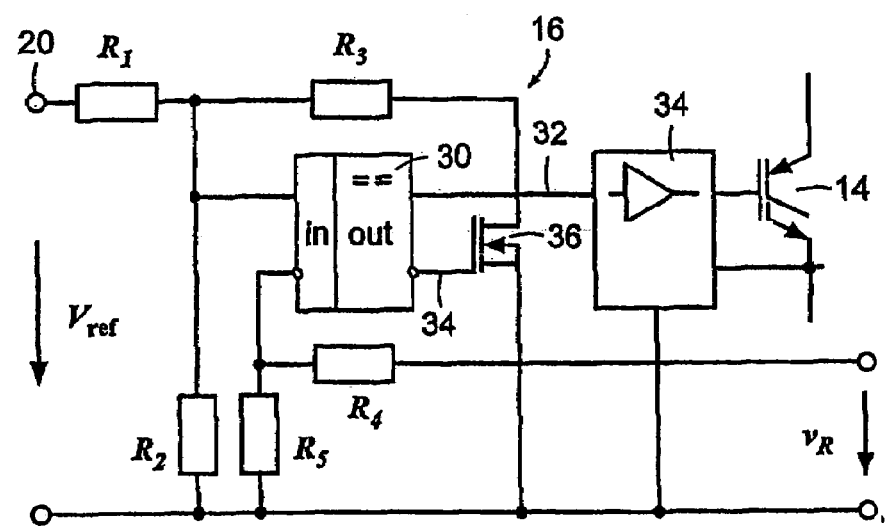
FIG. 2 is a schematic semi-block diagram of a control circuit for use in the circuit of FIG. 1.
Figure 4A:
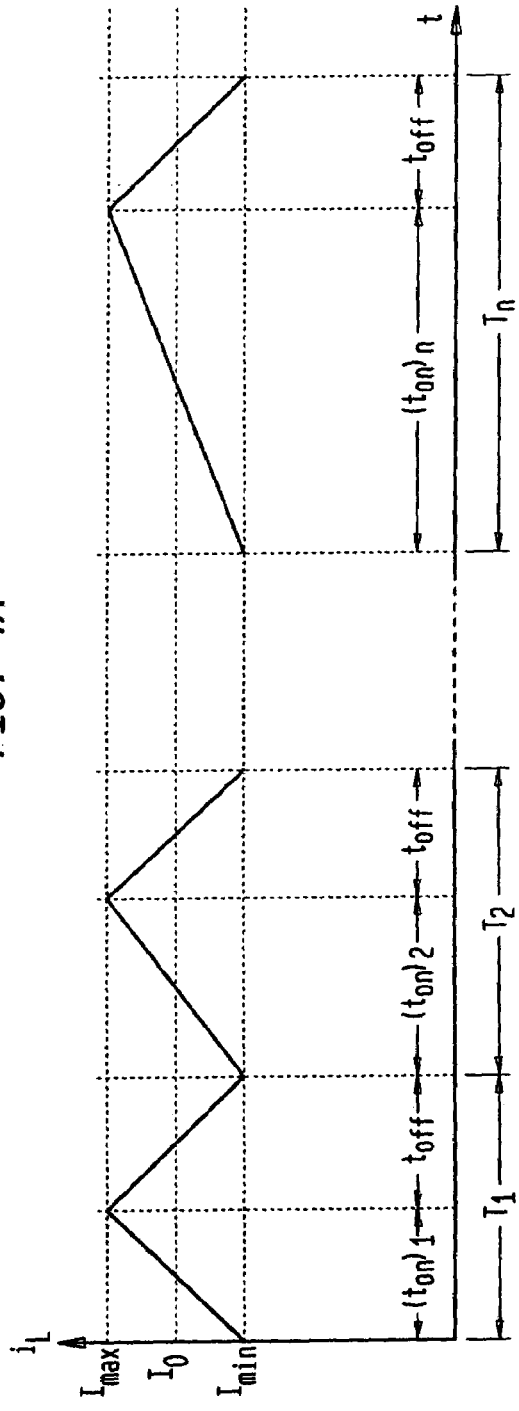
FIGS. 4A and 4B are diagrams illustrating the current/power across the lamp and the voltage across the capacitor respectively during successive on/off cycles of the transistor switch for a single flashlamp pulse.

FIG. 2 shows a control circuit suitable for use as switch control circuit 16. Referring to FIG. 2, it is seen that the reference voltage $V_{ref}$ at terminal 20 is applied through a voltage divider formed by resistors $R_1$ and $R_2$ to one input of a comparison circuit or comparator 30, for example a difference amplifier. The resulting voltage at the input to comparator 30 $V_{ref1}$ is desired maximum value of lamp current $I_{max}$. Current sensor feedback voltage $v_R$ is applied through a voltage divider consisting of resistors $R_4$ and $R_5$ to a second input of comparator 30. When $V_{ref1}$ is greater than $v_R$, comparator 30 generates an output on its direct output 32 which is applied through driver 34 to switch on power transistor 14, permitting capacitor C to discharge through inductor L and lamp 18. However, if $V_{ref1}$ is less than $v_R$, then comparator 30 generates an output only on its inverse output 34 which is applied to turn on transistor 36. The absence of output on direct output 32 causes transistor 14 to switch off. Transistor 36 being on causes resistor $R_3$ to be added to the voltage divider for $V_{ref}$, thereby reducing the voltage applied to the first input of comparator 30 to a $V_{ref2}$ proportional to a minimum current $I_{min}$ which is to flow through lamp 18. $I_{max}$ and $I_{min}$ are shown in FIG. 4A and are discussed in greater detail below.

Figure 3:
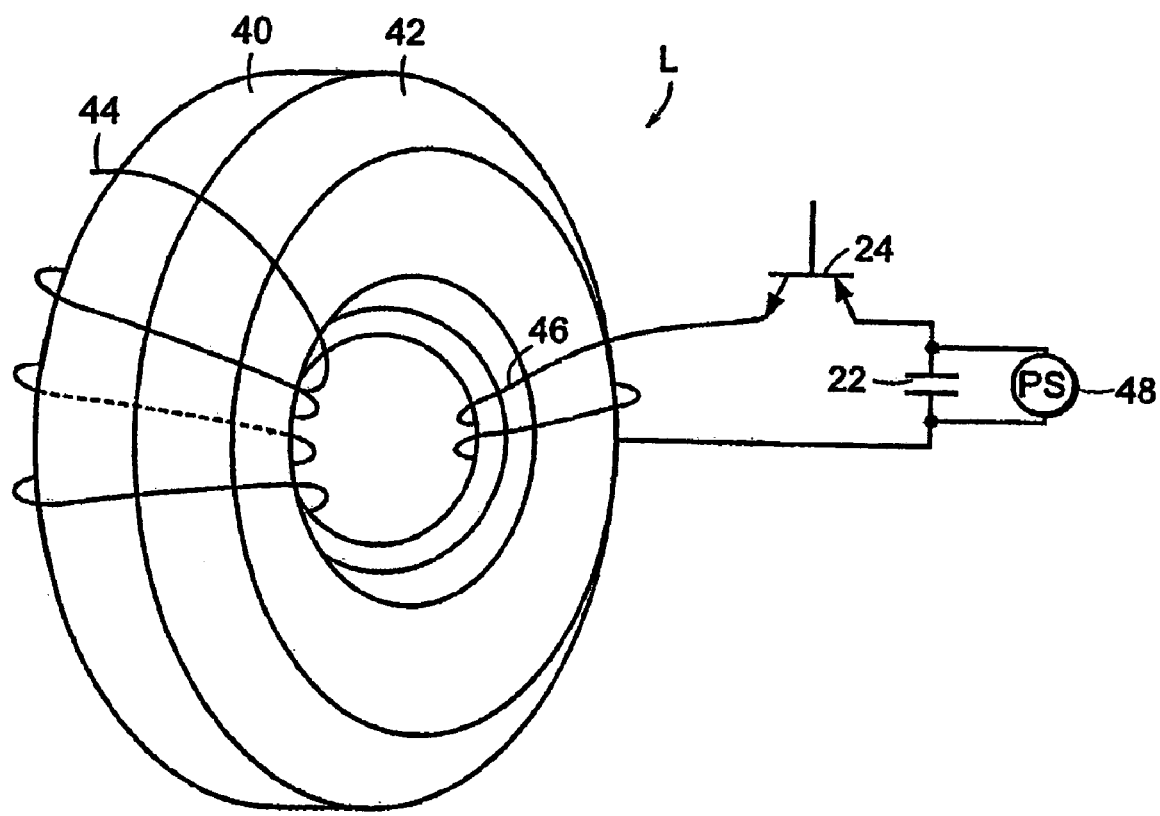
FIG. 3 is a partially schematic perspective view of a coil suitable for use in the circuit FIG. 1.

FIG. 3 is an enlarged diagram of an inductor L for an illustrative embodiment. This inductor being made up of a first core 40, a second core 42, a secondary winding 44 which function as a high voltage source during lamp triggering, and which also functions as an inductance coil or load winding, winding 44 being wound around both cores 40 and 42, and at least one primary winding 46, which is shown as being wound on both cores 40 and 42, but need be wound only on core 42. While only a single primary winding is shown in FIG. 3, this winding may be made up of several windings placed around the circumference of the core to provide proper coupling. As shown in FIG. 1, a triggering signal is applied to primary winding 46 from capacitor 22 under control of switch 24, which switch is preferably a semiconductor switch. The control input to transistor 24 is obtained from a control source which is not shown. Capacitor 22, which is typically relatively small, is charged from a power source 48 which would normally be the same as power source 12, but need not be the same.

For reasons to be discussed shortly, core 40 is of a magnetic material, for example powdered iron, which is non-saturating in the operating range of circuit 10, while core 42 is of a material having low losses at high frequency, for example a linear ferrite. While the cores 40 and 42 preferably have the same inner and outer dimensions, the thicknesses of the cores may be selected so that each is of an appropriate size to perform its desired function, as discussed in the following paragraphs.

OPERATION

As indicated earlier, in operation, in order to avoid premature failure of lamp 18 as a result of excessive vaporization of electrode material, acoustic shock effects on the lamp walls as the discharge goes directly to high current density arc mode or other causes, it is desirable that breakdown in flashlamp 18 be initially established by a voltage between the lamp electrodes of sufficient amplitude to establish only a weak discharge. This discharge may then be maintained with a low DC simmer current, permitting the much higher amplitude necessary to achieve the desired optical output to then be safely applied to the lamp. In the circuits of FIGS. 1 and 3, this low current density simmer mode discharge is initially established by use of the same coil 44 used for the inductor L in the main discharge or arc mode, thus simplifying and reducing the size, weight and cost of the circuit.

For an illustrative embodiment, coil 44 has approximately 25 windings or turns while primary coil 46 has approximately 2 turns, resulting in an over 10:1 step up ratio. Core 42 is of a size and material having low losses at high frequency, permitting transformation of the low voltage primary signal to the high voltage, fast rise time pulse necessary to break down the gas column in the lamp. The trigger pulse may for example have a duration of one ps. A core material suitable for core 42 is linear ferrite. Since core 42 has a very small volt second capacity, it saturates almost immediately when main voltages/currents are applied to the inductor, and its presence is therefore transparent for the lamp when in arc discharge mode. A voltage induced in winding 46 as a result of current flow through winding 44 is stepped down by for example a factor of 10 to 15 and is therefore not of concern.

Alternatively, the trigger circuit may use two primary windings, each with a dedicated switch, which operate alternately in opposite directions, thereby utilizing the material of core 42 at double its nominal flux capacity, and generating a bipolar trigger signal, further enhancing lamp breakdown.

When trigger switch 24 is activated, current flows in primary winding 46 for a period on the order of 1 microsecond. Core losses in powdered iron core 40 prevent coupling of the two windings by this core; however, the high resistivity and low core losses of ferrite core 42 permit effective coupling and transformation of the several hundred volt primary voltage to a several thousand volts secondary voltage level (for example 8 KV) necessary for lamp ionization. This results in lamp break-down which is then maintained by the DC simmer current from source 26. As indicated earlier, the current from simmer source 26 is generally less than an amp and may be on the order of a tenth of an amp or less.

For the main or arc mode discharge, capacitor C is charged to a value E from power source 12. Control circuit 16 is then enabled, for example by providing an enabling control signal to comparator 30 from an external control, for example a microprocessor, which is not shown. The control may for example operate in response to the detection of simmer current flow through the lamp. Since the current through lamp 18, and thus through resistance R, is initially substantially less than the $I_{max}$ current represented by $V_{ref2}$, comparator 30 generates an output on its direct output line 32 to turn on transistor 14, permitting capacitor C to discharge through inductor L and lamp 18. This causes a rapid increase in the current flow through lamp 18 and initiates the desired arc lamp discharge.

Figure 4B:
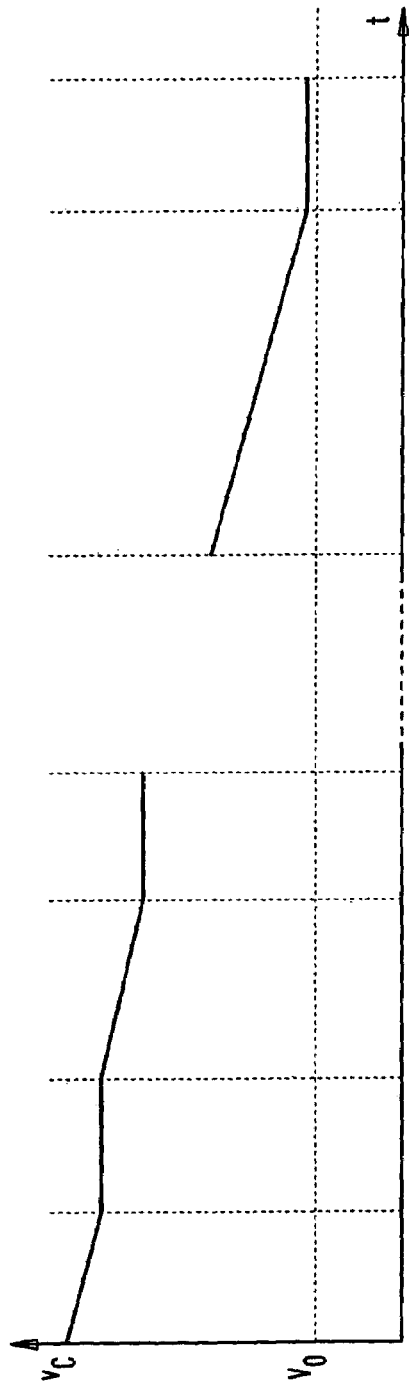

Current continues to increase in lamp 18 until the current is equal to $I_{max}$ (see FIG. 4a) at which time the output on direct output line 32 terminates and comparator 30 generates an output on its inverse output 34. This results in transistor 14 being turned off and transistor 36 being turned on. During the period that transistor 14 was turned on, the signal flowing through inductor L caused energy to be stored in the powdered iron core 40 of inductor L. When transistor 14 is turned off or opened, this energy discharges through path P, and thus through lamp 18 to maintain the desired discharge current therein. As indicated earlier, the turning on of transistor 36 results in a reduced reference voltage $V_{ref2}$ applied to the direct input of comparator 30 which is proportional to $I_{min}$ (FIG. 4a). Thus, transistor 14 remains off and transistor 36 remains on until the current through lamp 18 drops to $I_{min}$, at which time the outputs from comparator 30 again reverse, signal appearing on line 32 to turn on transistor 14 and being removed from line 34, thus turning off transistor 36. As seen in FIGS. 4A and 4B, this results in another drop in the voltage across capacitor C and results in the current across lamp 18 again increasing from $I_{min}$ to $I_{max}$. This cycle repeats until the desired pulse duration $t_p$ is reached, at which time the external control processor for example removes the enabling input from comparator 30. FIG. 4B shows the voltage across capacitor C remaining constant when transistor 14 is off or open, the control for charging of capacitor normally disabling charging during the arc mode discharge to prevent potential EMI between charge and discharge circuits. While this is not a limitation on the invention, charging the capacitor when in arc mode is of little consequence since the charging current is only on the order of one to two amps, while $I_0$, the average discharge current through the lamp may be up to 250 amps or more. FIG. 4A also shows the on time of transistor 14 increasing for successive cycles. This follows from the drop in voltage across the capacitor (see FIG. 4B) for each cycle of switch 14.

Each complete cycle of control circuit 16 lasts on the order of 25 microseconds for an illustrative embodiment, a time far beyond the volt-second interval capability of the linear ferrite used for core 42. The switching of transistor 14 thus occurs at tens to hundreds of kilohertz. Therefore, since the pulse durations $t_p$ contemplated for lamp 18 are generally in the millisecond range, and may, utilizing the teachings of this invention, be as long as 200 milliseconds or more without requiring an excessively large capacitor C, there can be hundreds of cycles of transistor switch 14 for each lamp pulse. In accordance with the teachings of this invention, this permits the shape of the pulse to be controlled by modifying $V_{ref}$ either upward or downward, in order to increase or decrease lamp output during the course of a pulse, and thus to vary pulse shape. A processor, for example a microprocessor (not shown), may be programmed to control the $V_{ref}$ applied to terminal 20 for each cycle of transistor 14 in order to achieve a desired pulse shape for lamp 18. $V_{ref}$ may also be controlled to achieve a desired color temperature for the lamp (i.e. to control the temperature of the lamp so as to maximize/minimize selected wavelengths in the lamp output). However, because of the voltage dividers used in setting the inputs to comparator 30, the relative current deviation $\alpha = \Delta I/I_0 = I_{max} - I_{min}/0.5 (I_{max} + I_{min})$ remains substantially constant, regardless of $V_{ref}$ and thus of the average current $i_0$ through the lamp. The values of the resistors R1-R5 can be selected in a manner to be described later to achieve the desired substantially constant $\alpha$ Operating with a substantially constant $\alpha$ has a number of advantages. First, the mathematical condition providing the substantially constant relative current deviation is $$E^2 - V_0^2 > \frac{2P_0}{C} t_p \quad (1)$$

where E is a voltage across capacitor C, $V_0$ is a voltage on the lamp, $P_0 = I_0 V_0$, $I_0$ is the average current on the lamp and $t_p$ is the duration of the flashlamp pulse. Since the mean current value $I_0$ does not depend on the initial voltage E on the capacitor and is set by the control circuit ($I_0 = 0.5 (I_{max} + I_{min})$), E may be set as high as 3-4 times the voltage on the lamp. Since energy utilization is a function of $(E^2-V^2/E^2)$ where V is the lamp voltage, this permits the maximum energy which can be delivered to the lamp during a pulse without power decrease to be approximately 90% of the energy stored in the capacitor [(i.e. $(E^2-V^2)/E^2$ becomes $(3^2-1^2)/3^2=8/9$ or $(4^2-1^2)/4^2=15/16$], this being substantially greater than the 20-50% energy utilization of the capacitor in prior art circuits. The more efficient utilization of capacitor energy permits greater lamp input/output for a given capacitor or the use of a smaller, less expensive capacitor for a given lamp output.

Further, while for prior circuits, the required value of the capacitor increases substantially linearly with increases in pulse duration, and normally becomes prohibitively large for pulses in excess of a few milliseconds, the circuit of this invention permits output pulses of up to several hundred milliseconds to be achieved without requiring any increase in capacitor value. In particular, for the circuit of FIG. 1, operating with $\Delta I/I_0$ being substantially constant, the capacitance C is given by $$C = \frac{2W}{E^2 - \left(\frac{Wk_0^2}{t_p}\right)^{\frac{2}{3}}} \quad (2)$$

where W is the total energy for the pulse of duration tp, and $k_0$ is the characteristic lamp impedance which is defined by the length "1" and the diameter "d" of the lamp discharge space ($k_0 = 1.28$ 1/d).

Thus, the capacitor C is substantially independent of pulse width or duration $t_p$ and, in fact, decreases slightly for increased $t_p$. By contrast, for most prior art circuits, the value of C increases linearly as a function $t_p$.

Still, another advantage of operating with a substantially constant $\Delta I/I_0$ is that the value of the inductance "L" is inverse to the value of current deviation $\Delta I$. Thus, by maintaining the substantially constant relative current deviation $\alpha$, the inductance value may be minimized, being substantially less than in some prior art circuits.

In order to achieve the substantially constant relative current deviation $\alpha$ discussed above, the following relationship for the resistor R1-R5 of FIG. 2 are required.

$$\frac{R_5}{R_4} < \frac{2}{\alpha} \quad (3a)$$

$$\frac{R_2}{R_1} = \frac{(R_5/R_4) \cdot (2+\alpha)}{2 - (R_5/R_4) \cdot \alpha} \quad (3b)$$

$$R_3 = \frac{R_2}{1+(R_2/R_1)} \cdot \left(\frac{1}{\alpha} - \frac{1}{2}\right) \quad (3c)$$

The above equations assume that the voltage $V_0$ corresponding to the mean value of lamp current $I_0$ is equal to $V_{ref}$, this condition simplifying resistor network balancing. If $R_5 = R_4$, then the calculation of resistors for a given ratio of relative current deviation $\alpha$ may be simplified to $$\frac{R_2}{R_1} = \frac{2+\alpha}{2-\alpha} \quad (4a)$$

-continued $$R_3 = \frac{R_2 \cdot (2-\alpha)^2}{8 \cdot \alpha} \quad (4b)$$

While the circuits described above can provide the indicated advantages so long as the lamp impedance Ko remains substantially constant, since illumination intensity is a function of average pulsed lamp power, where Ko varies during a light pulse, or between pulses, undesired variations in lamp intensity can also occur where lamp operation is controlled only in response to lamp current or lamp voltage. It has been found that this problem, caused by variations in lamp temperature or other causes, can result in variations of 10% to 20% or more between successive lamp pulses. These problems are overcome by the circuits of FIGS. 5-7. While to simplify these drawings, components such as power source 12, simmer source 26 and the components of FIG. 3 are not shown in these figures, these components could, if desired, be used with the embodiments of these figures for the same reasons and in the same way as for the prior embodiments.

Referring to FIG. 5, it is seen that, in additional to the missing parts discussed above, FIG. 5 also differs from FIG. 1 in that it includes a saturable inductor 50 between switch 14 and inductor coil L, a saturable inductor 51 in series with diode 5, a pair of series connected resistors 57a and 57b between the output side of inductor L and ground, and a high speed multiplier 59 having a voltage Vi indicative of lamp current as one input and a voltage Vv indicative of lamp voltage as its other input, the voltage Vv being taken at the junction of resistors 57a and 57b. While the voltage Vv is not equal to the lamp voltage, it is proportional to the lamp voltage, and any differences can thus be compensated for in multiplier 59, by other components of the circuit or in the selection of Vref. The output Vp from multiplier 59 is thus indicative of lamp power and is applied as the feedback input to switch control circuit 56.

Figure 5:
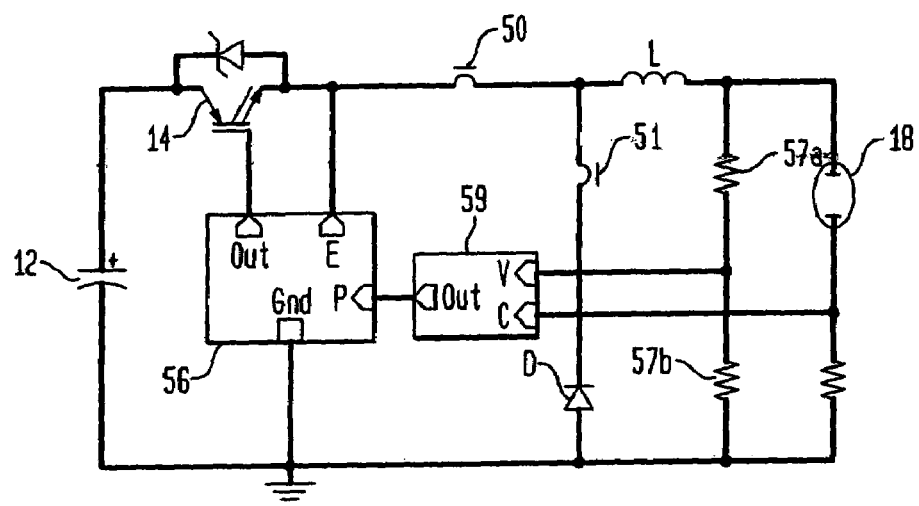
FIG. 5 is a schematic semi-block diagram of an alternative preferred circuit for practicing the teachings of the invention.

Saturable inductors 50 and 51 are provided in the circuit of FIG. 5 to protect switch 14 and diode D respectively, as well as other circuit components from current overload during each switch turn on/diode turn off transition. In particular, during the period the switch is turning on, which may be from tens to hundreds of nanoseconds, diode D is still fully saturated with charge carriers as a result of the direct current flow therethrough from inductor L through path P. The recovery or closing time for the diode can be several tens of nanoseconds for the fastest diodes. This results in a low resistance spurious path for current flow through the switch and in the reverse direction through the diode. This current flow, which can easily reach several hundred amps, can damage the switch, the diode and other components in this spurious current flow path. Inductors 50 and 51 provide a high impedance to the spurious currents during the transition period until diode D recovers and then saturate so as to disappear from the circuit during normal flow of current from switch 14 through inductor L and lamp 18.

Figure 6:
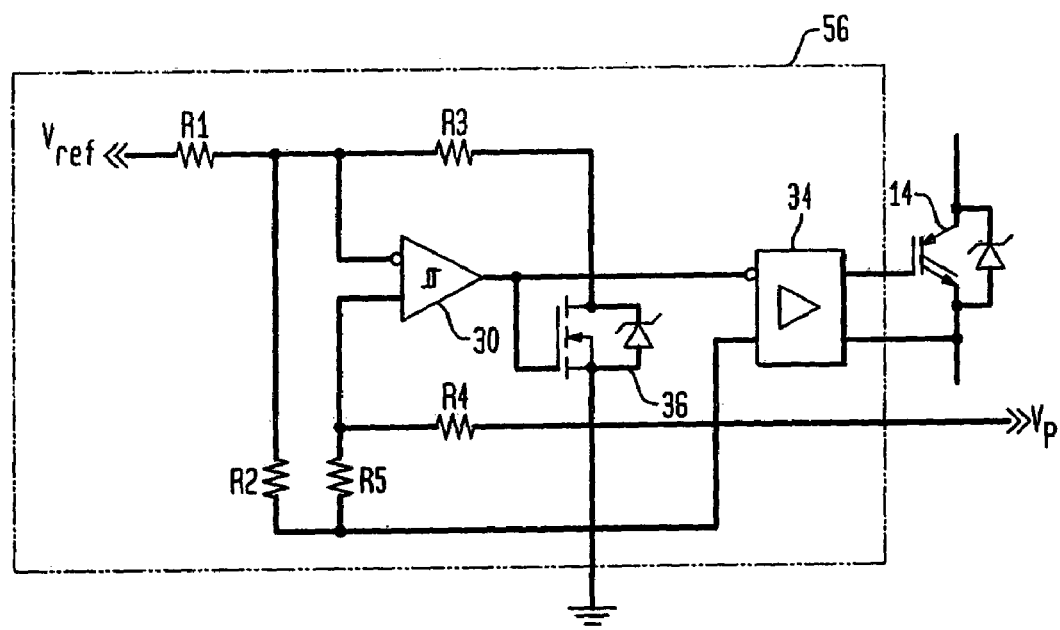
FIG. 6 is a schematic semi-block diagram of a control circuit for use in the circuit of FIG. 5.

FIG. 6 illustrates one embodiment of a control circuit 56 suitable for use in the circuit of FIG. 5, which circuit is the same as that of FIG. 2, and operates in substantially the same way as the circuit of FIG. 2, except that the input to the difference amplifier through resistor R4 is indicative of lamp power rather then lamp current and Vref is selected to achieve a desired average pulsed lamp power rather then a desired average lamp current. Switch 36 still functions in the same way to provide the desired Pmax/Pmin hysterisis. However, since control of the lamp is based on detected pulsed lamp power rather then lamp current, illumination can be maintained substantially constant regardless of variations in lamp impedance.

Figure 7:
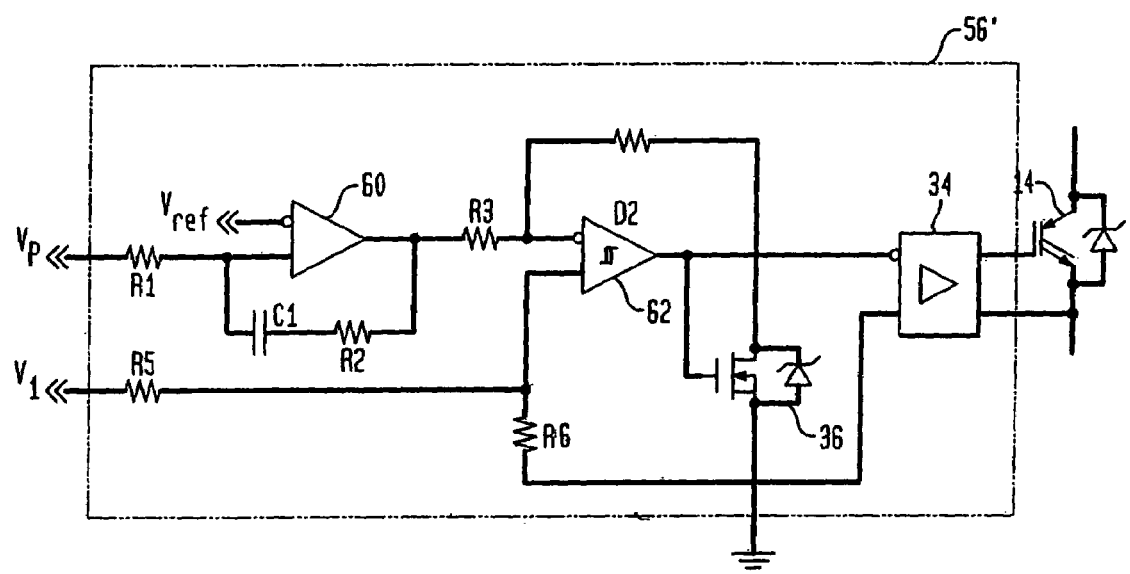
FIG. 7 is a schematic semi-block diagram of an alternative control circuit for use in the circuit of FIG. 5.

FIG. 7 illustrates an alternative control circuit 56' which may be advantageous in some applications. In this circuit, an error amplifier 60 is provided to which the Vp and Vref inputs are applied. The amplified power error output from error amplifier 60 is applied as one input to difference amplifier 62, the other input to this amplifier being a voltage indicative of lamp current. Switch 36 varies the error signal applied to amplifier 62 in the same way this component varies reference signals for prior embodiments to achieve the desired hysterisis. The remainder of the circuit functions the same as for prior embodiments.

The circuit of FIG. 7 may reduce the speed requirements for multiplier 59, permitting a significantly less expensive multiplier to be utilized. This results from the error amplifier strongly integrating power ripple in the Vp input signal. The circuit of FIG. 7 also greatly decreases high frequency noise caused by switching of power components in the circuit. This increases stabilizing properties of the circuit on the pulse "shelves", but can distort the edges of the pulses. Therefore, the circuit of FIG. 7 is preferable for applications where long pulses with high stability of peak power are required, such applications including, for example, certain medical applications, while the circuit of FIG. 6 may be preferable for applications having short pulses and good dynamic properties for programmable pulse shape.

While the comparator 30,62 is assumed to have a fixed hysteresis, so that an external reconfigurable voltage divider is required to vary the hysteresis, this is not a limitation on the invention and, if available, a comparator having a controlled or controllable variable hysteresis could be used, eliminating the need for the external voltage dividers. In addition, while the invention has been described above with reference to preferred embodiments, and various modification thereof have also been discussed, it is to be understood that these embodiments and the variations discussed are for purposes of illustration only and that the foregoing and other changes in form and detail may be made therein by one skilled in the art while still remaining within the spirit and scope of the invention which is to be defined only by the appended claims.

What is claimed is:

1. A drive circuit for a pulsed lamp, comprising:
    a first closed loop current path comprising a capacitor and an inductor coupled in series with the lamp, said capacitor being chargeable to a voltage sufficient, when applied across the lamp, to initiate lamp discharge,
    a second closed loop current path comprising the inductor coupled in series with the lamp,
    a controller circuit for enabling said capacitor to initiate the lamp discharge for generating a pulse of light,
    wherein said controller selectively activates said current paths one at a time during said pulse of light based on a current flowing through the lamp to control discharge of energy stored in the capacitor into the lamp so as to maintain current fluctuation through the lamp within a pre-selected range.

2. The circuit of claim 1, further comprising a semiconductor switch connected in series between said capacitor and said lamp to control discharge of energy stored in said capacitor into the lamp.

3. The circuit of claim 2, wherein said second current path comprises a one-way current switching device for providing a one-way flow of current from the inductor to the lamp so as to maintain current flow through the lamp when the first current path is inactive.

4. The circuit of claim 3, wherein said one-way current switching device comprises a diode.

5. The circuit of claim 2, further comprising a current sensor coupled to said lamp for detecting the current flowing therethrough.

6. The circuit of claim 5, wherein said controller receives a signal from said current sensor indicative of the current flowing through the lamp.

7. The circuit of claim 5, wherein said current sensor comprises a resistor connected at one end to a terminal of said lamp and at another end to ground such that the current flowing through said lamp induces a voltage across said resistor indicative of the current level.

8. The circuit of claim 7, wherein said controller comprises a comparator receiving at one input a reference voltage ($V_{ref}$) and at another input said voltage across the resistor, said comparator applying an output signal to said switch based on a difference between said input voltages to cause enabling or disabling of said switch.

9. A drive circuit for a lamp, comprising
an energy storage device connected in series with the lamp to provide the lamp with sufficient energy for generating an optical radiation pulse,
a switch coupled to the storage device and the lamp so as to permit discharge of energy stored in the device into the lamp when enabled and to block the discharge when disabled, and
a control circuit for selectively enabling or disabling said switch in response to power dissipated by said lamp to control discharge of energy from the storage device into the lamp so as to maintain a substantially constant ratio of power variation to an average power through the lamp during said pulse.

10. The circuit of claim 9, wherein said switch comprises a high speed semiconductor switch.

11. The circuit of claim 9, wherein said energy storage device comprises a capacitor.

12. The circuit of claim 11, further comprising an inductor connected in series with said capacitor and said lamp.

13. The circuit of claim 12, further comprising a diode disposed in a closed current path with said inductor and said lamp to provide a one-way current path from the inductor to the lamp for maintaining a current through the lamp when the switch is disabled.

14. The circuit of claim 13, further comprising a saturable inductor connected in series with said diode to inhibit current flow from the switch to the diode while the switch is transitioning from a disabled state to an enabled state or from an enabled state to a disabled state.

15. The circuit of claim 14, further comprising another saturable inductor connected in series with said switch to inhibit current flow through the switch during a transition period in which the diode is turning on and the switch is turning off.

* * * * *

(12) EX PARTE REEXAMINATION CERTIFICATE (7366th)
United States Patent
Inochkin et al.

(10) Number: US 7,274,155 C1
(45) Certificate Issued: Feb. 9, 2010

(54) FLASH LAMP DRIVE CIRCUIT

(75) Inventors: Mikhail Inochkin, St. Petersburg (RU); Vycheslav V. Togatov, St. Petersburg (RU); Peter O. Gnatyuk, St. Petersburg (RU)

(73) Assignee: Palomar Medical Technologies, Inc., Burlington, MA (US)

Reexamination Request:
No. 90/010,268, Sep. 4, 2008

Reexamination Certificate for:
Patent No.: 7,274,155
Issued: Sep. 25, 2007
Appl. No.: 11/091,270
Filed: Mar. 28, 2005

Related U.S. Application Data

(63) Continuation of application No. 10/600,167, filed on Jun. 20, 2003, now Pat. No. 6,888,319, which is a continuation-in-part of application No. 10/267,610, filed on Oct. 9, 2002, now abandoned, and a continuation of application No. 09/797,501, filed on Mar. 1, 2001, now abandoned.

(51) Int. Cl.
*H05B 41/16* (2006.01)

(52) U.S. Cl. .................. 315/247; 315/246; 315/308; 315/291; 315/274

(58) Field of Classification Search .................. None
See application file for complete search history.

(56) References Cited

U.S. PATENT DOCUMENTS 3,890,537 A    6/1975   Park et al. ............... 315/220 R
4,275,335 A * 6/1981   Ishida ...................... 315/241 P

OTHER PUBLICATIONS

Gottlieb, Irving, *Power Supplies, Switching Regulators, Inverters and Converters*, 1976, pp. 294–297.

* cited by examiner

*Primary Examiner*—My-Trang Ton

(57) ABSTRACT

The invention provides a power supply or drive circuit for a pulsed flashlamp which utilizes a two core component having common windings as both an inductor for arc mode drive and for breakdown triggering of the lamp. Discharge of a capacitor through the inductor and lamp is controlled by a high-speed semiconductor switch which is turned on and off by a suitable control, current flowing from the inductor through a one-way path including the lamp when the switch is off. The control maintains the ratio of the power variation through the lamp to the average power through the lamp substantially constant. The controls may also be utilized to control output pulse shape. Novel protective features are also provided for circuit components during turn on periods for the switch.

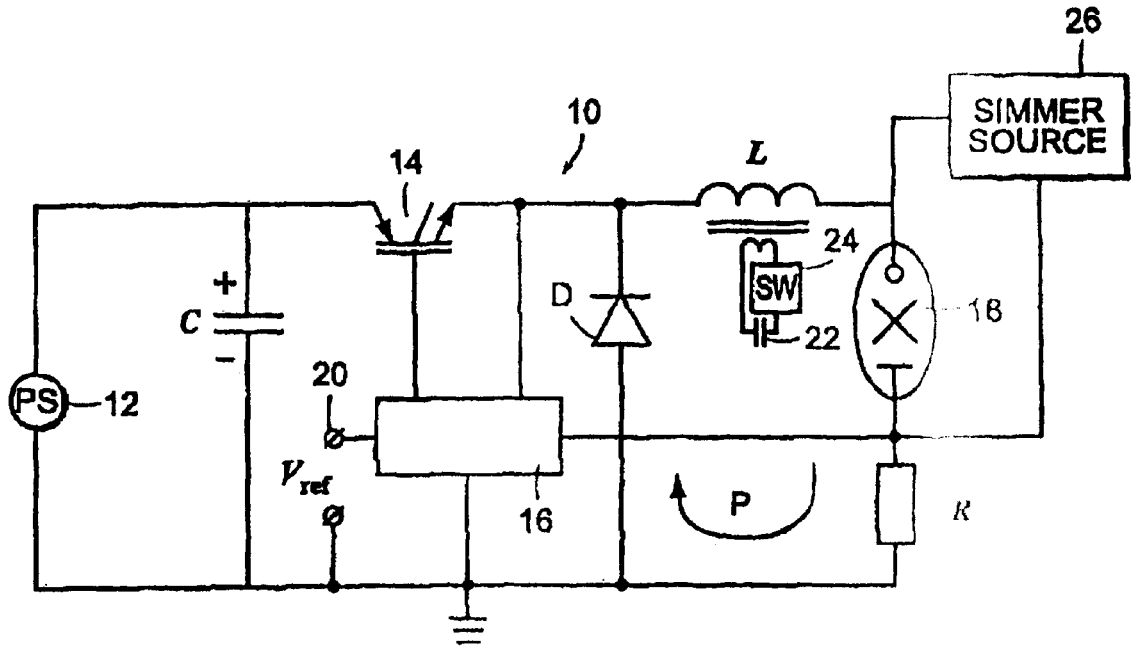

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7–8 is confirmed.

Claims 1–6, 9–13 are cancelled.

\* \* \* \* \*